United States Patent [19]

Brush et al.

[11] 4,306,942
[45] Dec. 22, 1981

[54] HYDROUS ALCOHOL DISTILLATION METHOD AND APPARATUS

[75] Inventors: Burke F. Brush, Harrison; Raphael Katzen, Cincinnati, both of Ohio

[73] Assignee: Raphael Katzen Associates International, Inc., Cincinnati, Ohio

[21] Appl. No.: 163,930

[22] Filed: Jun. 27, 1980

[51] Int. Cl.³ .................. B01D 3/14; C07C 29/80; C07C 31/08
[52] U.S. Cl. ........................ 203/19; 203/22; 203/23; 203/25; 203/42; 203/94; 203/DIG. 9; 203/DIG. 13; 203/DIG. 19; 202/158; 202/159; 202/174; 568/916
[58] Field of Search .................. 203/19, 22–26, 203/42, DIG. 13, DIG. 19, 73, 85, 99, 91, 94, 98, DIG. 9; 202/177, 180, 159, 154, 158, 172, 174, 156; 426/494; 568/916; 435/161; 44/53, 56

[56] References Cited

U.S. PATENT DOCUMENTS

| | | | |
|---|---|---|---|
| 1,702,495 | 2/1929 | Clapp . | |
| 1,744,261 | 1/1930 | Cooke | 203/22 |
| 1,822,454 | 9/1931 | Ricard et al. . | |
| 1,860,554 | 5/1932 | Ricard et al. . | |
| 2,017,067 | 10/1935 | Kraft . | |
| 2,080,167 | 5/1937 | Da Valle | 203/22 |
| 2,152,164 | 3/1939 | Wentworth | 203/75 |
| 2,276,089 | 3/1942 | Ragatz | 203/22 |
| 2,509,136 | 5/1950 | Cornell | 202/154 |
| 2,801,209 | 7/1957 | Mueller et al. | 203/85 |
| 3,406,100 | 10/1968 | Karafian | 203/85 |
| 3,420,748 | 1/1969 | Johnson et al. | 203/2 |
| 3,445,345 | 5/1969 | Katzen et al. | 203/25 |
| 3,990,952 | 11/1976 | Katzen et al. | 203/85 |
| 4,217,178 | 8/1980 | Katzen et al. | 203/19 |

FOREIGN PATENT DOCUMENTS

| | | |
|---|---|---|
| 876620 | 7/1971 | Canada . |
| 2346450 | 10/1977 | France . |
| 1310544 | 3/1973 | United Kingdom .......... 22/158 |

OTHER PUBLICATIONS

Chemical Process Industries, Shreve, 1945, pp. 653–654.
Elements of Fractional Distillation, Robinson and Gilliland, 1950, pp. 168–170.
"Controlled Heat Integrated Distillation Columns", Tyreus et al., Chemical Engineering Progress, Sep. 1976, pp. 59–66.

*Primary Examiner*—Wilbur L. Bascomb, Jr.
*Attorney, Agent, or Firm*—Merriam, Marshall & Bicknell

[57] ABSTRACT

An improved distillation method and apparatus are provided for recovering hydrous ethanol from fermentation or synthetic feedstocks. Substantial energy savings are realized by utilizing a pair of stripper-rectifier towers in which overhead vapors from one tower operating at a higher pressure supply the heat required for the other tower operating at a lower pressure and by preheating the feedstock in multiple heat exchange steps. The feedstock is split into two portions of unequal size, the larger portion being supplied to the higher pressure tower and the smaller portion to the lower pressure tower.

12 Claims, 10 Drawing Figures

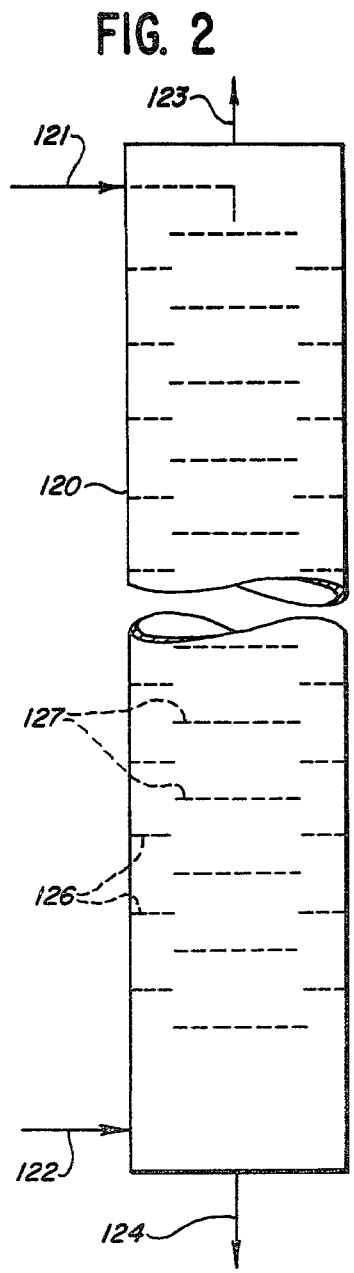
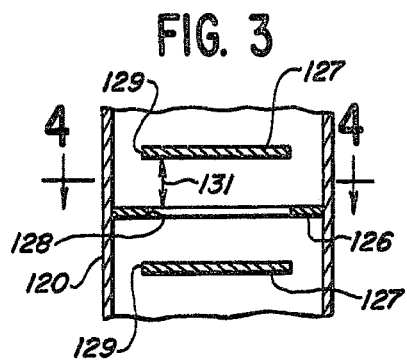
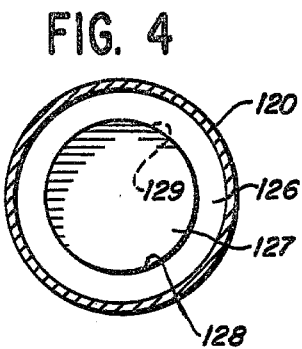
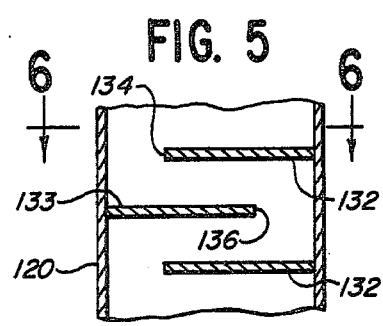
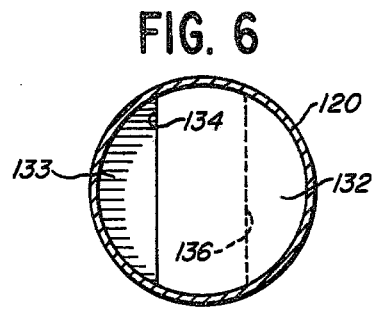
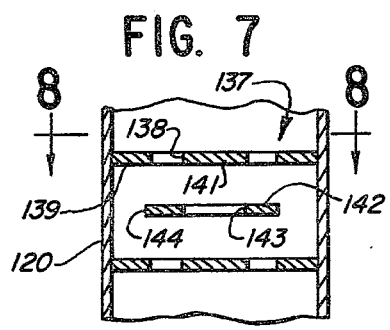
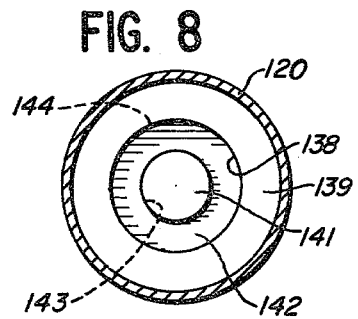
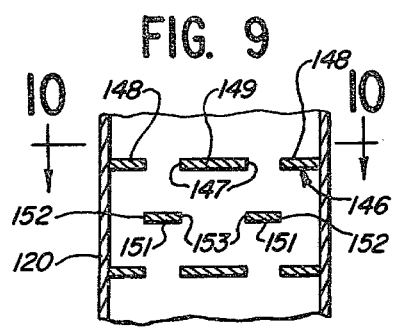
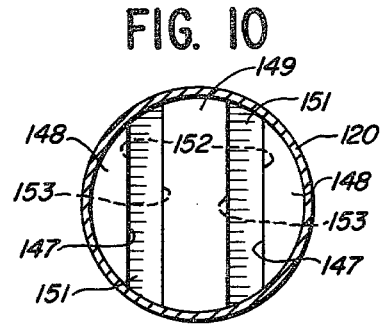

2

HYDROUS ALCOHOL DISTILLATION METHOD AND APPARATUS

This invention relates to a novel and improved integrated distillation system for recovering hydrous alcohol, specifically ethanol, from fermentation or synthetic feedstocks. Although not so limited, the invention is of particular significance in the production of hydrous ethanol for use as motor fuel.

BACKGROUND OF THE INVENTION

Hydrous ethanol, which is also known as industrial alcohol, may range from 170° to 195° U.S. proof (85 to 97.5 vol.% alcohol) but is most often commercially produced as 190° U.S. proof or 95 vol.% alcohol. This product has many uses in the chemical, pharmaceutical and beverage industries. For applications in which the water content of hydrous ethanol cannot be tolerated, it is necessary to produce so-called anhydrous ethanol which is usually 199° U.S. proof or 99.5 vol.% alcohol. For motor fuel purposes, either straight hydrous ethanol or straight anhydrous ethanol can be used directly, but only anhydrous ethanol can be mixed with gasoline because of phase separation problems encountered when water is present in gasohol (a blend of 10% anhydrous ethanol and 90% gasoline).

Hydrous ethanol may be separated from a dilute alcohol or beer feedstock by a stripping-rectifying operation in a single tower. The production of anhydrous ethanol, however, requires additional and more costly processing of hydrous ethanol. The most commonly used method comprises azeotropic distillation in a dehydrating tower using an entraining agent such as benzene so that the water in the hydrous ethanol is removed overhead as a ternary azeotrope and anhydrous ethanol is withdrawn as the bottom product. The azeotropic overhead is condensed and separated in a decanter from which an upper benzene-rich layer is returned to the dehydrating tower and a lower water-rich layer is fed to a stripping tower for recovery of benzene which is returned to the system.

Although hydrous ethanol is simpler and less costly to produce than anhydrous ethanol, there is still a pressing need to develop energy-efficient improvements in the distillation of the dilute alcohol feedstock, particularly where the hydrous ethanol is to be used as motor fuel. In the production of anhydrous ethanol by the usual azeotropic distillation, as described above, multiple distillation towers are required so that the opportunity is afforded to operate the first tower or beer still at a higher pressure than the other towers so that the overhead vapors from the first tower can be used as the heat supply for either or both of the other towers. This concept is disclosed in the Ricard et al U.S. Pat. Nos. 1,822,454 and 1,860,554.

In order to utilize the concept of heat re-use in the production of hydrous ethanol, it becomes necessary to split the stripping-rectifying step into two sections so that one tower can be operated at a higher pressure than the other while supplying dilute alcohol feedstock to the two towers in parallel.

SUMMARY OF THE INVENTION

Accordingly, the principal object of the present invention is to provide an improved distillation method and apparatus for recovering hydrous ethanol from fermentation or synthetic feedstocks which permits increased energy savings without sacrificing operating efficiency or product quality.

In general, the foregoing objective is achieved by providing a unique multiple stage heat exchange sequence for preheating the feedstock which is split and fed in parallel to a pair of stripper-rectifier towers operating at different pressures with overhead vapor from the higher pressure tower being used as the heat source for the lower pressure tower.

More specifically, in accordance with the present invention the feedstock is partially preheated by heat exchange in sequential stages with (1) the combined hydrous ethanol products from the two stripper-rectifier towers, (2) the overhead vapors from the lower pressure stripper-rectifier tower, and (3) steam condensate from the reboiler of the higher pressure stripper-rectifier tower. At this point the partially preheated feedstock is split into two portions of unequal size which are supplied in parallel to the two stripper-rectifier towers. The smaller portion receives its final preheat by heat exchange with bottoms or stillage from the lower pressure tower and is fed to that tower. The larger portion is further heated first by heat exchange with the hydrous ethanol product from the higher pressure tower and finally by heat exchange with the bottoms or stillage from the higher pressure tower and is then fed to that tower.

As a result, the steam consumption in our improved system is reduced to the order of from about 9 to about 13 pounds per U.S. gallon of hydrous ethanol product, dependent upon the ethanol content of the feedstock, which represents an energy saving of from about 30% to about 60% over the conventional practice using a single stripper-rectifier tower.

From an equipment viewpoint, the preferred form of the invention utilizes in the stripper section of at least the higher pressure stripper-rectifier tower the internal design and mode of operation described in British Pat. No. 1,310,544 and Canadian Pat. No. 876,620 which are incorporated herein by reference. With the baffle tray construction and critical vapor velocity relationships described therein the accumulation of scale and residue is retarded and the trays are to a large extent self-cleaning so that interruption of operation is held to a minimum.

Other features and advantages of the invention will be seen from the subsequent detailed description in conjunction with the accompanying drawings.

BRIEF DESCRIPTION OF THE DRAWING

FIG. 2 is a schematic representation of the preferred design for the stripper sections of the stripper-rectifier towers of the system;

FIG. 3 is a vertical sectional view through a portion of the tower shown in FIG. 2;

FIG. 4 is a horizontal sectional view taken along the line 4—4 of FIG. 3;

FIGS. 5, 7 and 9 are vertical sectional views similar to FIG. 3 and showing further embodiments of the tower; and FIGS. 6, 8 and 10 are horizontal sectional views taken along the corresponding lines of FIGS. 5, 7 and 9, respectively.

DETAILED DESCRIPTION

Figure 1:
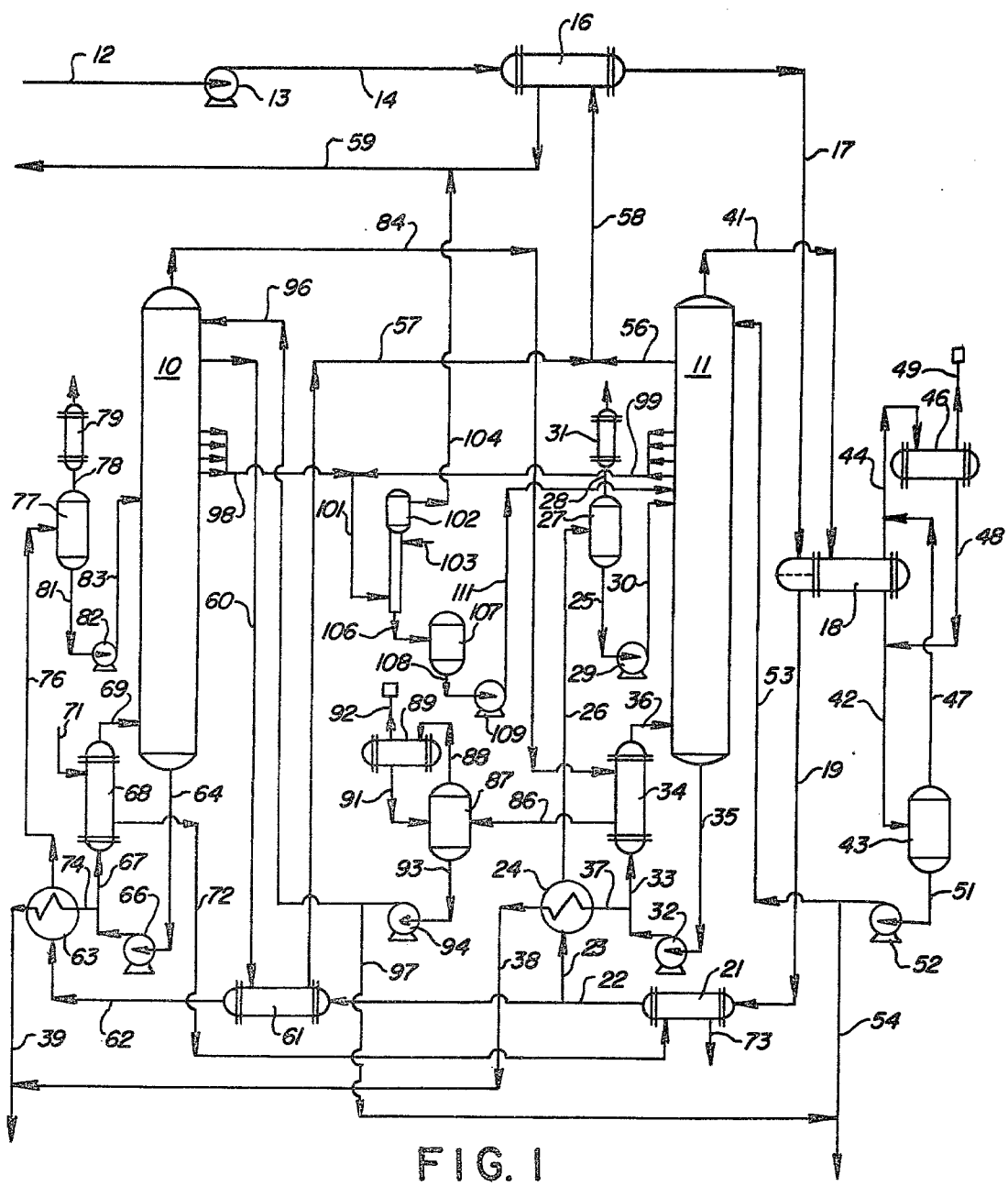
FIG. 1 is a diagrammatic flow sheet showing a distillation system comprising a preferred embodiment of the present invention.

Although any suitable fermented or synthetic feedstock can be used in practicing the invention, the distillation system illustrated in the drawing utilizes a fermented beer feedstock obtained by fermentation of a fermentable sugar material. The feedstock will usually contain from about 0.5 to about 20 wt.% ethanol, up to about 1.0 wt.% organic impurities, and up to about 10 wt.% dissolved and suspended solids. The system utilizes a pair of stripper-rectifier towers 10 and 11, the tower 10 being operated at a higher pressure than the tower 11.

The fermented beer at a temperature of from about 80° F. to about 100° F. is introduced through line 12 and pump 13 and is partially preheated in successive stages by passing through line 14 and product cooler 16, line 17 and condenser 18, and line 19 and heat exchanger or cooler 21, as described in more detail below. The partially preheated feedstock leaving the heat exchanger 21 through line 22 is then split into two streams of unequal size. The first feed stream passes through line 23 to a heat exchanger 24 where the final preheat is provided. This feed stream is the smaller of the two and preferably comprises less than 50 wt.% but not less than about 30 wt.% of the total feed. The preheated feed stream then passes through line 26 to a degassing drum 27 where dissolved carbon dioxide resulting as a by-product of the fermentation is removed. In the case of synthetic feedstock from direct hydration synthesis, dissolved ethylene would be removed in drum 27. The feed stream then passes to the midsection of the lower pressure stripper-rectifier tower 11 through line 25, pump 29, and line 30 to the top of the stripping section of the tower. The dissolved gas removed from the feed stream in drum 27 is discharged through line 28 and a vent condenser 31, and any condensate is returned through line 28 to drum 27.

Heat is supplied to the lower pressure tower 11 by recycling a portion of the tower bottoms stream through line 35, pump 32, line 33, reboiler 34, and line 36. The balance of the bottoms stream passes through line 37 and heat exchanger 24 where it is cooled to approximately its atmospheric boiling point before passing through lines 38 and 39 to waste or stillage concentration. Thus, the final preheat for the smaller feed stream is supplied in heat exchanger 24 by heat exchange with the bottoms or stillage from the lower pressure tower 11.

The overhead vapors are removed from the lower pressure tower 11 through line 41 and are condensed in condenser 18 while at the same time supplying a portion of the preheat to the feed stream. The condensate flows from condenser 18 through line 42 to a reflux drum 43. The condenser 18 is also connected by a line 44 to a vent condenser 46, and a line 47 communicates between the vapor space in the reflux drum 43 and the line 44. Any condensate formed in the vent condenser 46 is returned to the reflux drum 43 by line 48 connecting with line 42. Uncondensible gases are discharged to the atmosphere from the vent condenser 46 through vent means 49. Reflux is withdrawn from the reflux drum 43 through line 51 and is returned by a pump 52 through line 53 to the top tray of the tower 11 except for a small heads draw which is removed from the system through line 54.

Since the overhead from the tower 11 contains the low-boiling impurities in the feedstock, particularly acetaldehyde, the continuous heads draw through line 54 removes these impurities from the system and avoids their accumulation and possible adverse effect on the quality of the hydrous ethanol product particularly when intended for motor fuel use. The product stream is removed as a side draw somewhat below the top of the tower 11, e.g. from five to ten trays below the top of the tower, but if the lower boiling impurities are found to be acceptable, the product stream may be removed from the reflux line 53. The hydrous ethanol product passes through line 56 and is combined with the hydrous ethanol product stream in line 57 from the higher pressure tower 10, as described below. The combined hydrous ethanol product stream passes through line 58 to the product cooler 16 and then through line 59 to product storage.

The remaining or second feed stream is the larger of the two feed streams and preferably comprises more than 50 wt.% but not more than about 70 wt.% of the total feed. This stream passes through line 22, beyond the intersection with the first feed stream withdrawal at line 23, to a heat exchanger 61 where additional preheat is supplied to the feed stream by means of the hydrous ethanol product stream removed from a point somewhat below the top of the higher pressure tower 10, e.g. from five to ten trays below the top of the tower. The hydrous ethanol product passes from the tower 10 through line 60 to the heat exchanger 61 and then through line 57 to be combined with the other hydrous ethanol product stream from tower 11, as previously described.

The final preheat for the larger feed stream is supplied by heat exchange with the bottoms or stillage from tower 10. Thus, the feed stream is passed from the heat exchanger 61 through line 62 to a heat exchanger 63. A bottoms stream from the tower 10 is withdrawn through line 64 and is passed by a pump 66 and line 67 to a reboiler 68 and recycled through line 69 back to the tower 10. The recycled bottoms stream is heated in the reboiler 68 by means of steam introduced through line 71, and the steam condensate passes through line 72 to heat exchanger 21 for preheating the feed, as previously described. The condensate is withdrawn from the heat exchanger 21 through line 73. A portion of the recycled bottoms stream is withdrawn from line 67 through line 74 and passes through the heat exchanger 63 to preheat the second feed stream and then passes through line 39 where it is combined with the bottoms stream in line 38 from the tower 11.

The preheated second feed stream passes from the heat exchanger 63 through line 76 to a degassing drum 77 where dissolved carbon dioxide, or ethylene in the case of synthetic feedstock, is removed and discharged through line 78 and a vent condenser 79. Any condensate formed in the vent condenser 79 is returned through line 78 to the drum 77. The feed stream passes from the drum 77 through line 81 to a pump 82 and is fed through line 83 to the top of the stripping section of the tower 10.

As heretofore explained, in order to conserve thermal energy the invention relies on the overhead vapors from the stripper-rectifier tower 10 as the heating source for the stripper-rectifier tower 11. Thus, it is necessary that the tower 10 be operated at a higher pressure (e.g. atmospheric pressure to 100 psig) than the tower 11 (e.g. sub-atmospheric pressure to 50 psig). In the preferred embodiment of the invention the tower 10 is operated at about 50 psig while the tower 11 is operated at substantially atmospheric pressure. Overhead vapors under pressure are removed from the higher pressure tower 10 through line 84 and are passed to reboiler 34 where the vapors are condensed to supply heat to the tower 11 through the recirculating bottoms stream as already described. The condensate passes from the reboiler 34 through line 86 to a reflux drum 87. The vapor space in the reflux drum 87 is connected by a line 88 to a vent condenser 89. Any condensate formed in the vent condenser 89 is returned to the reflux drum 87 through line 91, and uncondensible gases are discharged to the atmosphere through vent means 92. Reflux is withdrawn from the reflux drum 87 through line 93 and is returned by a pump 94 through line 96 to the top tray of the tower 10 except for a small heads draw which is removed through line 97 and is combined with the heads draw removed through line 54 from the reflux supply for the tower 11.

Higher boiling impurities such as alcohols and esters (fusel oils) are formed as extraneous products of the fermentation (or synthesis) process, and in the present invention these impurities are removed as one or more liquid side streams which pass through lines 98 and 99 from intermediate portions of the stripper-rectifier towers 10 and 11, respectively. The fusel oil draws are normally made at an alcohol concentration between about 100° and about 160° U.S. proof. The side streams are combined and are introduced through line 101 to the lower end of a fusel oil washer-decanter 102 where they are washed countercurrently with cold water introduced at 103. The fusel oils are decanted as an upper layer which is withdrawn through line 104. The separated fusel oil layer has significant fuel value and may be blended into the hydrous ethanol product being sent to storage through line 59. The lower aqueous layer containing ethanol washed out of the fusel oil passes through line 106 to an accumulator drum 107 and is withdrawn through line 108 and pumped by a pump 109 through line 111 to a side entry point somewhat above the main feed entry point (at line 30) of the stripper-rectifier tower 11.

The hydrous ethanol product is removed as a liquid side-draw stream somewhat below the top of the stripper-rectifier tower 10, e.g. five to ten trays below the top of tower, but if the lower boiling impurities are found to be acceptable, the product stream may be removed from the reflux line 96. As previously described, the product stream from the tower 10 is used to preheat the second feed stream by passing through line 60 to the heat exchanger 61 before passing through line 57 to be combined with the product stream in line 56 from the tower 11.

From the foregoing it will be seen that the invention accomplishes substantial reductions in energy consumption by recovering and utilizing to the fullest extent the heat content of various process streams of the system. Thus, the overhead vapors from the higher pressure stripper-rectifier tower 10 supply all, or substantially all, of the heat requirements for the lower pressure stripper-rectifier tower 11, and the only heat input to the system under most circumstances is the steam used in the reboiler of the higher pressure tower 10. The feedstock is preheated in a plurality of stages. First, the feedstock is preheated sequentially in the combined product cooler 16, the overhead condenser 18 for the tower 11, and the heat exchanger 21 which is supplied with steam condensate from the reboiler for tower 10. To permit heating of the tower 11 substantially entirely by the overhead vapors from the tower 10, the partially preheated feed stock is divided into two feed streams of unequal size. The smaller of the two streams is fed to the tower 11 after receiving its final preheat from the bottoms withdrawn from tower 11. The larger of the two feed streams is fed to the tower 10 after being preheated by the heat content of the product stream removed from the tower 10 and receiving its final preheat from the bottoms withdrawn from the tower 10.

The net result of the economies effected by the present invention is that the steam consumption (usually only for heating the tower 10) is reduced to the order of from about 9 to about 13 pounds per U.S. gallon of hydrous ethanol product, dependent upon the alcohol content of the feedstock. The outstanding heat economy of the system is shown by the fact that the total heat requirement is very close to the sensible heat difference between the feed stream and the stillage stream, i.e. virtually no heat leaves the system in the cooling water. A corollary benefit is that an almost negligible amount of cooling water is required as compared to a conventional distillation system using a single stripper-rectifier tower.

Since the tower 10 is ordinarily operated under superatmospheric pressure, the stripping section of the tower preferably utilizes the baffle tray design and mode of operation described in British Pat. No. 1,310,544 and Canadian Pat. No. 876,620 in order to minimize scaling and fouling of the tower. In the aforesaid patents the section of the tower below the feed tray is provided with a plurality of vertically spaced baffles in the form of smooth surfaced plate members which are imperforate, except for specified relatively large open areas for the passage of fluids, and are free of the usual flow-obstructing protuberances such as weirs, seals, bubble caps, downcomers, and the like. The vapor-liquid contacting action is obtained in the vertical spaces between successive baffles.

Although other baffle designs may be used, the preferred structure comprises a "disk and donut" baffle configuration consisting of a plurality of vertically-spaced annular or ring-shaped baffle members and a plurality of circular or disk-shaped baffle members interposed in vertically spaced relation between the annular baffle members. The outer peripheries of the annular baffle members engage the inner surface of the tower and the inner peripheries or edges of these baffle members define circular open areas. The circular baffle members overlie and are in substantial axial alignment with the open areas in the adjacent annular baffle members. An annular open area is defined between the edge of each circular baffle member and the wall of the tower, and the open areas of adjacent baffle members are transversely offset so that the ascending gas or vapor phase must traverse a tortuous path with repeated changes of direction in passing upwardly through the open areas of the baffles.

The vertical space between successive baffles is such that the liquid phase which overflows the edges of the open areas of the baffles is contacted with a relatively high velocity gas or vapor phase so as to effect substantially complete dispersion of the down-flowing curtain of liquid into discrete droplets or an aerated liquid or froth, depending upon the surface tension relationship of the gas or vapor and the liquid. Thereafter, as the gas or vapor containing the entrained liquid droplets passes upwardly through the open areas of the baffles, the velocity is substantially decreased so that the major part of the liquid droplets will coalesce and drop back to the next lower baffle thereby keeping the net entrainment to a minimum. The separated gas or vapor, containing only a moderate amount of entrained liquid, then passes upwardly through the next vertical space between baffles and the dispersing or frothing effect is repeated. By means of the repeated velocity changes between successive sets of baffles, a multiplicity of contacts are effected whereby selected components of the gas or vapor will be transferred into the descending liquid or selected components of the liquid phase will be desorbed or stripped and transferred into the ascending gas or vapor stream.

In FIGS. 2–4, a stripper section 120 is shown having an inlet 121 for introducing a liquid or slurry into the upper portion of the stripper section for downward passage therethrough and an inlet 122 for introducing a gas or vapor into the lower portion of the stripper section for upward passage therethrough. The stripper section 120 is also provided at is upper end with a gas or vapor outlet 123 and at its lower end with an outlet 124 for the liquid or slurry.

As best seen in FIGS. 3 and 4, the internal baffle arrangement consists of a plurality of vertically-spaced annular or ring-shaped baffle members 126 and a plurality of circular or disk-shaped baffle members 127 interposed in vertically spaced relation between the annular baffle members 126. Both the baffle members 126 and the baffle members 127 are essentially planar, imperforate, and smooth-surfaced and are free from the usual weirs, seals, downcomers, caps or other flow-obstructing protuberances. The outer peripheries of the annular baffle members 126 engage the inner surface of the tower 120, and the inner peripheries or edges of the baffle members 126 define circular baffle openings 128. Suitable seals (not shown) may be provided at the outer peripheries of the baffle members 126, if desired, to prevent by-passing of fluids between the baffles and the tower wall. The baffle members 126 and 127 are mounted coaxially within the tower 120 by any suitable support means (not shown) so that the circular baffle members 127 overlie and are in substantial axial alignment with the openings 128 in the adjacent annular baffle members 126. An annular opening 129 is defined between the edge of each circular baffle member 127 and the wall of the tower 120. For the sake of economy, a pair of annular and circular baffle members 126 and 127 are preferably made out of a single sheet metal plate so that the diameter of the opening 128 in the baffle member 126 is essentially the same as the diameter of the circular baffle member 127. However, it should be understood that these dimensions may be different, if desired. Also, as will be evident from FIG. 3, the openings 128 and 129 of adjacent baffle members are transversely offset so that the ascending gas or vapor phase must traverse a tortuous path with repeated changes of direction in passing upwardly through the open areas of the baffles.

Effective multi-phase contact is obtained by proper design and selection of the vertical spacing between adjacent baffle members, as indicated by the arrow 131 in FIG. 3, and by proper design of the size of the circular and annular baffle openings 128 and 129, respectively, so as to obtain a relatively high velocity of the gas or vapor when flowing essentialy horizontally through the curtain of liquid overflowing the baffle edges and a considerably reduced velocity of the gas or vapor when flowing essentially vertically through the baffle openings.

In the preferred mode of operation of the baffle tray tower the flow rate of the gas or vapor phase is correlated with the vertical spacing between adjacent baffles and with the open areas of the baffles such that the horizontal velocity factor $f_h$ between adjacent baffles is within the range of from 0.20 to 0.80 feet per second and the vertical velocity factor $f_v$ in the open areas of the baffles is substantially less than the horizontal velocity factor $f_h$ and is also within the range of from 0.10 to 0.40 feet per second. The velocity factors are determined in accordance with the following equations:

$$f_h = U_h \left( \frac{\rho v}{\rho L - \rho v} \right)^{\frac{1}{2}}$$

$$f_v = U_v \left( \frac{\rho v}{\rho L - \rho v} \right)^{\frac{1}{2}}$$

where $U_v$ is the velocity in feet per second of the gas or vapor phase passing through the open areas of the baffles, $U_h$ is the velocity in feet per second of the gas or vapor phase passing through the descending liquid phase between adjacent baffles, $\rho v$ is the density in pounds per cubic foot of the ascending gas or vapor phase at the temperature and pressure in the tower, and $\rho v$ is the density in pounds per cubic foot of the descending liquid phase at the temperature in the tower. In general, the horizontal velocity factor will be on the order of twice the vertical velocity factor, and because of the intensive agitation caused by contact of rising vapors against descending liquid, the baffle trays are to a large extent self-cleaning so that interruption of operations is at a minimum.

In addition to observing the critical velocity factors and selecting the proper dimensions for the internal baffle system of the tower, it is also essential to provide a sufficient flow of liquid or slurry through the inlet 121 so as to maintain a predetermined level on each of the baffle members which overflows the edges of the baffle openings 128 and 129 to insure a continuous curtain of showering liquid from baffle to baffle. Dependent upon the tower diameter, a liquid flow in the range of from about 20 to about 500 gals./1 hr. for each inch of baffle opening edge is adequate to develop a stable and relatively uniform liquid crest on the baffles over a relatively wide range of tower diameter, e.g. from about 18 inches to about 240 inches. For example, in a tower having a diameter in the range of 18 to 24 inches, a liquid overflow from the baffles of about 20 gals./hr. per inch of baffle edge results in a crest height of about ¼ inch, which is generally the minimum practical crest height for a tower of this size. On the other hand, in the tower diameter range of 60 to 240 inches, a liquid overflow rate of 500 gals./hr. per inch of baffle edge results in a crest height of about 2 inches. For most operations, a practical median crest height of about 1 inch is indicated.

Although the "disk and donut" baffle configuration heretofore described is highly useful and frequently preferred, various other baffle configurations may also be use. For example, FIGS. 5 and 6 show a tower 120 equipped with segmental shaped baffle members 132 and 133 which extend partially across the tower to define segmental openings 134 and 136 which, in this instance, are disposed at diametrically opposite portions of the tower cross-section. Thus, the baffles 132 and 133 extend in substantial overlapping relationship so that the tower is characterized by a marked side-to-side flow of liquid and gas or vapor phases.

In FIGS. 7 and 8, the tower 120 is designed to obtain a split internal flow by the use of multiple-piece baffles such as the circular baffle plates, indicated generally at 137, which have annular openings 138 so as to define an outer annular or ring-shaped baffle portion 139 and a central disk-shaped baffle portion 141 lying in a common plane. Interposed in vertically spaced relation between the baffle members 137 are annular or ring-shaped baffle member 142 arranged so as to overlie the annular openings 138 in the adjacent baffle members 137. The baffle members 142 thus define a central circular baffle opening 143 and an outer annular baffle opening 144.

In FIGS. 9 and 10 the tower 120 is again provided with multiple-piece baffles to give a split flow relationship. In this instance, however, one set of baffles, indicated generally at 146, consists of circular plates having transversely spaced chordal openings 147 so that each baffle 146 consists essentially of a pair of oppositely spaced segmental portions 148 and an intermediate chordal portion 149 all laying in a common plane. The other baffles interposed between the baffles 146 each comprise a pair of transversely spaced chordal strips 151 arranged so as to overlie the chordal openings 147 in the adjacent baffles 146. The edges of the spaced chordal baffle portions 151 thereby define at their outermost edges a pair of segmental baffle openings 152 and at their innermost edges a central chordal baffle opening 153.

For purposes of further illustrating the invention, the following non-limiting specific example is provided.

EXAMPLE

A distillation system as shown in the drawing and described above is used to recover 190° U.S. proof hydrous ethanol for motor fuel used from a fermented feedstock at a production rate of 54 million gallons per year.

The beer feed having a temperature of about 90° F. and an ethanol content of about 10 vol.% is processed at a rate of about 580,000 lb/hr. The feed is preheated in three preliminary stages. In the first stage the feed is heated from about 90° F. to about 94° F. in the cooler 16 by means of 190° proof product ethanol at a rate of about 45,000 lb/hr, the ethanol being cooled from about 175° F. to about 95° F. In the second stage, the feed is heated to about 164° F. in the preheater-condenser 18 by means of overhead vapors from the tower 11 having a temperature of about 173° F. In the third stage, the feed is heated to about 180° F. in the heat exchanger 21 by means of steam condensate from the reboiler 68 at a flow rate of about 63,000 lb/hr, the condensate being cooled from about 340° F. to about 190° F.

At this point the beer feed splits into two streams of unequal size.

The larger of the two streams comprising about 320,000 lb/hr or about 55 wt.% of the total beer feed passes through the preheater 61 which also cools the ethanol product stream from the tower 10. This exchanger cools about 25,000 lb/hr of ethanol product from about 250° F. to about 180° F. while heating the feed stream from about 180° F. to about 183° F. This beer stream then receives its final preheat in the heat exchanger 63 from the bottoms stream from the tower 10. In this exchange, about 295,000 lb/hr of the bottoms stream is cooled from about 303° F. to about 204° F. while the beer stream is heated from about 183° to about 274° F. This beer stream then passes through the degassing drum 77 where carbon dioxide is released and then finally enters the stripper-rectifier tower 10. The smaller of the two streams comprising about 260,000 lb/hr or about 45 wt.% of the total beer feed receives its final preheat in heat exchanger 24 from the bottoms stream from the tower 11. In this exchange, about 239,000 lb/hr of the bottoms stream is cooled from about 220° F. to about 200° F. while the beer stream is heated from about 180° F. to about 198° F. This beer stream then passes through the degassing drum 27 where carbon dioxide is released and then finally enters the stripper-rectifier tower 11.

The stripper-rectifier tower 10 operates at a pressure of about 50 psig. All of the steam input to the process, 63,000 lb/hr of 150 psig steam, goes to the reboiler 68 of the tower 10. The overhead vapors from the tower 10 are at a temperature of about 250° F. and are condensed in the reboiler 34 of the stripper-rectifier tower 11. The tower 11 operates at atmospheric pressure with a bottoms temperature of 220° F., giving a 30° F. temperature differential across its reboiler.

Fusel oil side draws are taken through lines 98 and 99 and are sent to the common fusel oil washer 102 where ethanol is extracted out with water and recycled. The fusel oils are decanted and then mixed with the product ethanol stream by lines 104 and 59 since the ethanol is to be used for motor fuel. Product ethanol is removed through lines 56 and 60 several trays from the top of each tower so that a removal of low boiling impurities can be made by the heads draw streams 54 and 97 if desired. For motor fuel use the removal of low boiling impurities may be necessary to avoid vapor lock problems, but for other end uses, the removal of such impurities by purge streams may not be necessary.

The steam consumption amounts to only about 9.2 pounds per U.S. gallon of hydrous ethanol product, as compared with a typical steam consumption of from about 18 to about 25 pounds per gallon when using a conventional single stripper-rectifier system.

Although the invention has been described with particular reference to the preferred embodiment illustrated in the drawing, it will be understood that various modifications may be made without departing from the scope of the invention as defined in the appended claims.

We claim:

1. A distillation method for recovering hydrous ethanol from a dilute ethanol-containing feedstock which comprises:
   (a) partially preheating a feedstock stream;
   (b) splitting the partially preheated feedstock stream into two feed streams of unequal size;
   (c) further preheating both the larger and the smaller of said feed streams;
   (d) introducing the preheated feed streams in parallel into a pair of stripper-rectifier towers;
   (e) maintaining a higher pressure in the stripper-rectifier tower receiving the larger feed stream than in the stripper-rectifier tower receiving the smaller feed stream;
   (f) condensing steam to supply the heat required in the higher pressure stripper-rectifier tower;
   (g) condensing overhead vapors from the higher pressure stripper-rectifier tower to supply the heat required in the lower pressure stripper-rectifier tower, and returning the resultant condensate as reflux to said higher pressure stripper-rectifier tower;

(h) condensing overhead vapors from said lower pressure stripper-rectifier tower, and returning the resultant condensate as reflux to said lower pressure stripper-rectifier tower;

(i) withdrawing a hydrous ethanol product stream from the upper portion of said higher pressure stripper-rectifier tower, and cooling the same;

(j) withdrawing a hydrous ethanol product stream from the upper portion of said lower pressure stripper-rectifier tower;

(k) combining the cooled hydrous ethanol product stream from step (i) with the hydrous ethanol product stream from step (j);

(l) cooling the combined hydrous ethanol product stream; and (m) withdrawing a bottoms stream from each of said stripper-rectifier towers and separately cooling the same;

(n) said partial preheating of said feedstock stream being effected in stages by means of the heat obtained in cooling step (1), in condensing step (h), and by heat exchange with stream condensate from condensing step (f);

(o) said further preheating of said smaller feed stream being effected by means of the heat obtained in step (m) during cooling of the bottoms stream from said lower pressure stripper-rectifier tower; and (p) said further preheating of said larger feed stream being effected in stages by means of heat obtained in cooling step (i) and in step (m) during cooling of the bottoms stream from said higher pressure stripper-rectifier tower.

2. The method of claim 1 wherein the larger of said feed streams comprises more than 50 wt.% but not more than about 70 wt.% of the total feed, and the smaller of said feed streams comprises less than 50 wt.% but not less than about 30 wt.% of the total feed.

3. The method of claim 1 wherein the condensate streams in steps (g) and (h) are returned as reflux to the respective towers, except for the removal of a heads draw from each of said condensate streams to avoid accumulation of low-boiling impurities in the combined hydrous ethanol product stream.

4. The method of claim 1 wherein at least one fusel oil side draw containing higher boiling impurities is removed from an intermediate portion of each of said stripper-rectifier towers, said fusel oil side draws are combined and washed with water, a fusel oil layer is separated from an aqueous ethanol-containing layer, and said aqueous ethanol-containing layer is returned to said lower pressure stripper-rectifier tower.

5. The method of claim 4 wherein said fusel oil layer is blended with said combined hydrous ethanol product stream.

6. The method of claim 4 wherein the hydrous ethanol product stream is withdrawn from the corresponding stripper-rectifier tower at a location below the point of return of said reflux but above the point of removal of said fusel oil side draw.

7. The method of claim 1 wherein the pressure in said higher pressure stripper-rectifier tower is from atmospheric pressure to about 100 psig and the pressure in said lower pressure stripper-rectifier tower is from subatmospheric to about 50 psig.

8. The method of claim 7 wherein the pressure in said higher pressure stripper-rectifier tower is about 50 psig and the pressure in said lower pressure stripper-rectifier tower is about atmospheric pressure.

9. The method of claim 1 wherein at least said higher pressure stripper-rectifier tower contains a plurality of vertically spaced baffles comprising substantially smooth surfaced imperforate plate members which are free of weirs, seals, bubble caps, downcomers and the like, said baffles being arranged to provide transversely offset open areas so that ascending gas or vapor phase traverses a tortuous path upwardly through the tower as liquid phase descends therethrough; and the flow rate of said gas or vapor phase is correlated with the vertical spacing between adjacent baffles and with the open areas of said baffles such that the horizontal velocity factor $f_h$ between adjacent baffles is within the range of from 0.20 to 0.80 feet per second and the vertical velocity factor $f_v$ in the open areas of said baffles is substantially less than the horizontal velocity factor $f_h$ and is within the range of from 0.10 to 0.40 feet per second, said velocity factors being determined in accordance with the following equations:

$$f_h = U_h \left( \frac{\rho_v}{\rho_L - \rho_v} \right)^{\frac{1}{2}}$$

$$f_v = U_v \left( \frac{\rho_v}{\rho_L - \rho_v} \right)^{\frac{1}{2}}$$

where $U_v$ is the velocity in feet per second of the gas or vapor phase passing through the open areas of said baffles, $U_h$ is the velocity in feet per second of the gas or vapor phase passing through the descending liquid phase between adjacent baffles, $\rho_v$ is the density in pounds per cubic foot of the ascending gas or vapor phase at the temperature and pressure in the tower, and $\rho_l$ is the density in pounds per cubic foot of the descending liquid phase at the temperature in the tower;

whereby the liquid phase overflows the baffle edges as a continuous curtain and is dispersed into discrete droplets or froth by high velocity gas or vapor phase in the vertical spaces between adjacent baffles and a decreased gas or vapor phase velocity is obtained in the open areas of the baffles permitting the major part of the liquid droplets or froth to coalesce and separate from the ascending gas or vapor phase.

10. In the method of recovering hydrous ethanol from a dilute ethanol-containing feedstock wherein said feedstock is split into two feed streams, said feed streams are introduced in parallel into a pair of stripper-rectifier towers, a higher pressure is maintained in one of said towers than in the other, said one tower is heated by condensation of steam in the reboiler of said one tower, overhead vapors from said one tower are condensed to supply the heat required in said other tower, and a hydrous ethanol product stream and a bottoms stream are removed from each of said towers; the improvement which comprises:

(a) partially preheating said feedstock in stages by means of the heat obtained by cooling the combined hydrous ethanol product streams, by condensation of the overhead vapors from said other tower, and by heat exchange with steam condensate from said reboiler of said one tower;

(b) further preheating the feed stream being introduced into said other tower by means of heat obtained by cooling of the bottoms stream from said other tower; and (c) further preheating the feed stream being introduced into said one tower by means of heat obtained by cooling the hydrous ethanol product stream from said one tower, and by cooling of the bottoms stream from said one tower.

11. The method of claim 10 wherein the feed stream introduced into said one tower comprises more than 50 wt.% but not more than about 70 wt.% of the total feed, the feed stream introduced into said other tower comprises less than 50 wt.% but not less than about 30 wt.% of the total feed, the pressure in said one tower is from atmospheric pressure to about 100 psig, and the pressure in said other tower is from sub-atmospheric to about 50 psig.

12. A distillation apparatus for recovering hydrous ethanol from a dilute ethanol-containing feedstock comprising, in combination: means for partially preheating a dilute ethanol-containing feedstock stream; means for splitting the partially preheated feedstock stream into two feed streams of unequal size; means for further preheating both the larger and the smaller of said feed streams; a higher pressure stripper-rectifier tower; a lower pressure stripper-rectifier tower; means for introducing the larger of said feed streams into said higher pressure tower; means for introducing the smaller of said feed streams into said lower pressure tower; first reboiler means for condensing steam to supply the heat required in said higher pressure tower; steam condensate cooler means for cooling the steam condensate from said first reboiler means; second reboiler means for condensing overhead vapors from said higher pressure tower to supply the heat required in said lower pressure tower; means for returning the resultant overhead vapor condensate as reflux to said higher pressure tower; condenser means for condensing overhead vapors from said lower pressure tower; means for returning the resultant overhead vapor condensate as reflux to said lower pressure tower; means for withdrawing a hydrous ethanol product stream from an upper portion of said higher pressure tower; first product cooler means for cooling said hydrous ethanol product stream from said higher pressure tower; means for withdrawing a hydrous ethanol product stream from the upper portion of said lower pressure tower; means for combining the cooled hydrous ethanol product stream from said first cooler means with the hydrous ethanol product stream from said lower pressure tower; second product cooler means for cooling the combined hydrous ethanol product streams; means for withdrawing a bottoms stream from each of said towers; and separate bottoms cooler means for cooling the bottoms stream from each of said towers; said means for partially preheating said feedstock stream comprising means for passing said feedstock in heat exchange relation through said second product cooler means and then through said condenser means and then through said steam condensate cooler means; said means for further preheating said smaller feed stream comprising means for passing said smaller feed stream in heat exchange relation through said bottoms cooler means for cooling the bottoms stream from said lower pressure tower; and said means for further preheating said larger feed stream comprising means for passing said larger feed stream in heat exchange relation through said first product cooler means and then through said bottoms cooler means for cooling the bottoms stream from said higher pressure tower.

* * * * *